(12) United States Patent
Kurnik

(10) Patent No.: US 7,680,603 B2
(45) Date of Patent: Mar. 16, 2010

(54) SYSTEMS AND METHODS FOR DETERMINING REAL-TIME PCR CYCLE THRESHOLDS USING A ROTATION TRANSFORMATION

(75) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 982 days.

(21) Appl. No.: 11/078,692

(22) Filed: Mar. 11, 2005

(65) Prior Publication Data

US 2006/0204972 A1  Sep. 14, 2006

(51) Int. Cl.
*G01N 33/48* (2006.01)
*C12P 19/34* (2006.01)

(52) U.S. Cl. .................................... 702/19; 435/91.2
(58) Field of Classification Search .................. None
See application file for complete search history.

(56) References Cited

U.S. PATENT DOCUMENTS 6,303,305 B1   10/2001   Wittwer et al.

OTHER PUBLICATIONS

Bronshtein and Sendyayev (1997), "Handbook of mathematics," Springer (pp. 196-197).*
Wolvich et al., "The Determination of Implicit Polynomial Canonical Curves," vol. 20 (1998) pp. 1080-1090.*
Wilhelm et al., "SoFar: Software for Fully Automatic Evaluation of Real-Time PCR Data," Biotechniques, vol. 34 (2003) pp. 324-332.*
Pitas, "Fast Alogrithms for Running Ordering and Max/Min Calculation," IEEE Transactions on Circuits and Systems (1989) vol. 36, pp. 795-804.*
Bar, Tzachi, "Kinetic Outlier Detection (KOD) in real-time PCR," Nucleic Acids Research, 2003, vol. 31, No. 17, 7pp.
Bernard, Philip S., "Cancer Diagnostics Review, Real-Time PCR Technology for Cancer Diagnostics," Clinical Chemistry, 2002, vol. 48, No. 8, pp. 1178-1185.
Goll, Rasmus, et al. "Evaluation of absolute quantitation by nonlinear regression in probe-based real-time PCR," BMC Bioinformatics, 2006, vol. 7, No. 107, pp. 1-11.
Higuchi, Russell, "Kinetic PCR Analysis: Real-time Monitoring of DNA Amplification Reactions," Nature Publishing Group, 1993, vol. 11, pp. 1026-1030.
Peirson, Stuart, et al., "Experimental validation of novel and conventional approaches to quantitative real-time PCR data analysis," Nucleic Acids Research ,Oxford University Press, 2003, vol. 31, No. 14, pp. 1-7.
Ramakers, Christian, et al. "Assumption-free analysis of quantitative real-time polymerase chain reaction (PCR) data," Neuroscience Letters, 2003, vol. 339, pp. 62-66.
Vu, Huong L., et al. "A method for quantification of absolute amounts of nucleic acids by (RT)-PCR and a new mathematical model for data analysis," Nucleic Acids Research, Oxford University Press, 2000, vol. 28, No. 7, pp. 1-9.
Whitney, Scott E. "Principles of Rapid Polymerase Chain Reactions: Mathematical Modeling and Experimental Verification," Computational Biology and Chemistry, 2004, vol. 28, pp. 195-209.
Wilhelm, Jochen, "Validation of an Algorithm for Automatic Quantification of Nucleic Acid Copy Numbers By Real-Time Polymerase Chain Reaction," Analytical Biochemistry, 2002, vol. 317, pp. 218-225.

* cited by examiner

*Primary Examiner*—John S Brusca
*Assistant Examiner*—Anna Skibinsky
(74) *Attorney, Agent, or Firm*—Townsend and Townsend and Crew LLP; Gerald T. Gray

(57) ABSTRACT

Systems and methods for determining the elbow or Ct value in a real-time, or kinetic, PCR amplification curve data set. The PCR data set may be visualized in a two-dimensional plot of fluorescence intensity vs. cycle number. A rotation transform is applied to the data set to rotate the data about a defined coordinate such as the origin so that the data point representing the Ct value becomes a minimum or a maximum along the intensity axis. The data point representing the elbow or Ct value of the PCR curve is identified, and this data point is then rotated back and the cycle number of the data point is returned or displayed.

21 Claims, 10 Drawing Sheets

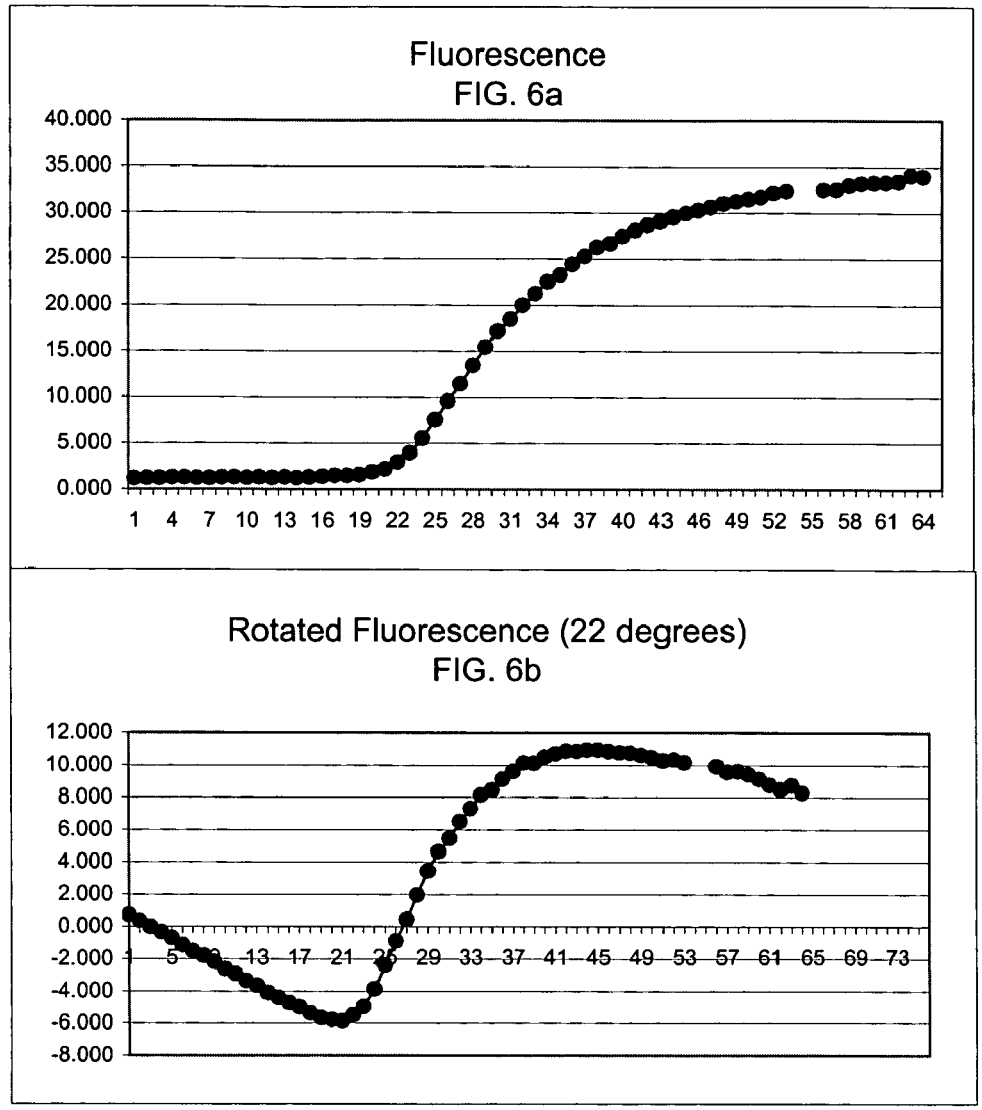
Coordinates of minimum in rotated growth curve: (20.18, -5.85)
Coordinates of Ct: (20.90, 2.13)
Ct: 20.90

| Cycle Number | Fluorescence | Rotated Cycle Number (22 degrees) | Rotated Fluorescence (22 degrees) |
|---|---|---|---|
| 1 | 1.164 | 1.363 | 0.705 |
| 2 | 1.196 | 2.302 | 0.359 |
| 3 | 1.189 | 3.227 | -0.022 |
| 4 | 1.251 | 4.177 | -0.339 |
| 5 | 1.259 | 5.107 | -0.706 |
| 6 | 1.188 | 6.008 | -1.147 |
| 7 | 1.185 | 6.934 | -1.523 |
| 8 | 1.284 | 7.898 | -1.806 |
| 9 | 1.286 | 8.827 | -2.179 |
| 10 | 1.214 | 9.727 | -2.620 |
| 11 | 1.290 | 10.682 | -2.925 |
| 12 | 1.219 | 11.583 | -3.365 |
| 13 | 1.317 | 12.547 | -3.649 |
| 14 | 1.232 | 13.442 | -4.102 |
| 15 | 1.309 | 14.398 | -4.405 |
| 16 | 1.358 | 15.344 | -4.735 |
| 17 | 1.484 | 16.318 | -4.992 |
| 18 | 1.471 | 17.240 | -5.379 |
| 19 | 1.557 | 18.200 | -5.674 |
| 20 | 1.859 | 19.240 | -5.768 |
| 21 | 2.174 | 20.285 | -5.851 |
| 22 | 2.956 | 21.506 | -5.500 |
| 23 | 3.938 | 22.800 | -4.965 |
| 24 | 5.526 | 24.323 | -3.867 |
| 25 | 7.522 | 25.997 | -2.391 |
| 26 | 9.545 | 27.682 | -0.890 |
| 27 | 11.389 | 29.300 | 0.446 |
| 28 | 13.417 | 30.987 | 1.951 |
| 29 | 15.414 | 32.663 | 3.428 |
| 30 | 17.128 | 34.232 | 4.642 |
| 31 | 18.418 | 35.642 | 5.464 |
| 32 | 19.937 | 37.139 | 6.498 |
| 33 | 21.202 | 38.539 | 7.296 |
| 34 | 22.518 | 39.960 | 8.141 |
| 35 | 23.261 | 41.165 | 8.456 |
| 36 | 24.401 | 42.520 | 9.139 |
| 37 | 25.308 | 43.786 | 9.605 |
| 38 | 26.275 | 45.076 | 10.126 |
| 39 | 26.658 | 46.147 | 10.108 |
| 40 | 27.484 | 47.383 | 10.499 |
| 41 | 28.097 | 48.540 | 10.693 |
| 42 | 28.707 | 49.695 | 10.883 |
| 43 | 29.093 | 50.767 | 10.866 |
| 44 | 29.580 | 51.877 | 10.943 |
| 45 | 29.983 | 52.955 | 10.943 |
| 46 | 30.293 | 53.999 | 10.856 |
| 47 | 30.619 | 55.048 | 10.783 |
| 48 | 30.990 | 56.114 | 10.753 |
| 49 | 31.253 | 57.140 | 10.621 |
| 50 | 31.502 | 58.160 | 10.478 |
| 51 | 31.692 | 59.159 | 10.280 |
| 52 | 32.163 | 60.262 | 10.341 |
| 53 | 32.375 | 61.269 | 10.164 |

FIG. 6c

| | | | |
|---|---|---|---|
| 54 | 32.515 | 62.248 | 9.918 |
| 55 | 32.543 | 63.186 | 9.570 |
| 56 | 32.986 | 64.279 | 9.606 |
| 57 | 33.193 | 65.284 | 9.423 |
| 58 | 33.286 | 66.246 | 9.135 |
| 59 | 33.305 | 67.180 | 8.778 |
| 60 | 33.407 | 68.146 | 8.498 |
| 61 | 34.074 | 69.323 | 8.742 |
| 62 | 33.969 | 70.211 | 8.270 |

FIG. 6c (cont.)

SYSTEMS AND METHODS FOR DETERMINING REAL-TIME PCR CYCLE THRESHOLDS USING A ROTATION TRANSFORMATION

BACKGROUND OF THE INVENTION

The present invention relates generally to systems and methods for processing data representing sigmoid or growth curves, and more particularly to systems and methods for determining characteristic cycle threshold (Ct) or elbow values in real-time PCR amplification curves.

The Polymerase Chain Reaction (PCR) is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in real-time PCR, or kinetic PCR, to facilitate detection and quantification of the amplification process.

A typical kinetic PCR curve as shown in FIG. 1, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of quenched fluorescently labeled hybridization probes which only emit fluorescence signals after they are bound to a target nucleic acid sequence and subsequently degraded by the 5' to 3' nuclease activity of a DNA polymerase. Other examples include fluorescent signals generated during nucleic acid amplification where fluorescent dyes bind to double-stranded DNA and experience an increase in their fluorescence quantum yield.

For a typical kinetic PCR growth curve, identifying a transition point referred to commonly as the elbow value or cycle threshold (Ct) value is extremely useful for understanding characteristics of the PCR amplification process. The Ct value may be used as a measure of efficiency of the PCR process. For example, a defined signal threshold is determined for all reactions to be analyzed. Then the number of cycles (Ct) required to reach this signal threshold is determined for the target nucleic acid as well as for reference nucleic acids such as a standard or housekeeping gene. The absolute or relative copy numbers of the target molecule can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value 20 in FIG. 1 would be in the region of cycle number 30.

A more precise elbow value in a kinetic PCR curve can be determined using several existing methods. For example, various methods determine the actual value of the elbow (Ct) as the value where the fluorescence reaches a predetermined signal level called the AFL (arbitrary fluorescence value). Other methods use the cycle number where the second derivative of fluorescence vs. cycle number reaches a maximum. All of these methods have drawbacks. For example, derivative methods are sensitive to outlier (noisy) data, and the AFL approach is sensitive to changes in the average baseline fluorescent level in the pre-elbow PCR cycles. Furthermore, these algorithms typically have many parameters that are often difficult to optimize. This results in a trade-off between sensitivity and false positives that reduces the effectiveness of these algorithm approaches.

Therefore, it is desirable to provide new systems and methods for determining the elbow value in curves, such as sigmoid-type curves, and kinetic PCR curves in particular, that overcome these drawbacks and others.

BRIEF SUMMARY OF THE INVENTION

The present invention provides novel, efficient methods for determining characteristic transition values such as elbow values on sigmoid or growth-type curves. In one implementation, the methods of the present invention are particularly useful for determining the cycle threshold (Ct) value in kinetic PCR amplification curves.

According to the present invention, a method for determining the elbow or Ct value in a kinetic PCR amplification curve data set is provided. The PCR data set may be visualized in a two-dimensional plot of fluorescence intensity vs. cycle number. A rotation transform is applied to the data set to rotate the data about a defined coordinate such as the origin so that the data point representing the Ct value becomes a minimum or a maximum along the intensity axis. The data point representing the elbow or Ct value of the PCR curve is identified, and this data point is then rotated back and the cycle number of the data point is returned or displayed.

According to an aspect of the present invention, a computer-implemented method is provided for determining a specific point of interest in a region of a curve. The method typically includes receiving a data set representing a curve, the data set including a plurality of data points each having a pair of coordinate values, wherein if viewed in a two-dimensional coordinate system the data set includes a region of interest. The method also typically includes applying a first rotational transformation to at least a portion of the data set including the region of interest to produce a transformed data set, identifying a data point in the transformed data set having at least one minimum coordinate value, and applying a second rotational transformation, inverse to the first transformation, to the identified data point. The method further typically includes re-determining at least one coordinate value of the identified data point, wherein the re-determined coordinate value of the identified data point represent a specific point of interest in the curve. In one aspect, the curve is an amplification curve for a kinetic Polymerase Chain Reaction (PCR) process, and the specific point of interest represents the elbow or cycle threshold (Ct) value for the kinetic PCR curve. One or both of the re-determined coordinates of the identified data point are returned or displayed.

According to another aspect of the present invention, a computer readable medium is provided that includes code for controlling a processor to determine a cycle threshold (Ct) value in a kinetic PCR amplification curve. The code typically includes instructions to receive a data set representing a kinetic PCR amplification curve, the data set including a plurality of data points each having a pair of coordinate values, wherein the data set includes data points in a region of interest which includes the Ct value. The code also typically includes instructions to apply a first rotational transformation to at least the portion of the data set including the region of interest to produce a transformed data set, identify a data point in the transformed data set having at least one minimum coordinate value, apply a second rotational transformation, inverse to the first transformation, to the identified data point, and thereafter re-determine at least one coordinate value of the identified data point, wherein the re-determined coordinate value of the identified data point represents the Ct value for the PCR curve.

According to yet another aspect of the present invention, a kinetic PCR system is provided. The system typically includes a PCR analysis module that generates a PCR data set representing a kinetic PCR amplification curve, the data set including a plurality of data points each having a pair of coordinate values, wherein the data set includes data points in a region of interest which includes a cycle threshold (Ct) value. The system also typically includes an intelligence module adapted to process the PCR data set to determine the Ct value by applying a first rotational transformation to at least the portion of the data set including the region of interest to produce a transformed data set, identifying a data point in the transformed data set having at least one minimum coordinate value, applying a second rotational transformation, inverse to the first transformation, to the identified data point, and thereafter re-determining at least one coordinate value of the identified data point, wherein the re-determined coordinate value of the identified data point represents the Ct value for the PCR curve. The intelligence module may include a processor in a computer system connected to or separate from the kinetic PCR analysis module, or it may include a processor directly coupled to the kinetic PCR analysis module, e.g., both components may comprise a kinetic PCR thermocycler.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 6 shows an example of a data set for an amplification curve processed according to the present invention. FIG. 6c is a table including the data set values (cycle number and fluorescence intensity) of the amplification curve shown in FIG. 6a, and the values of the rotated cycle number and rotated fluorescence when rotated by 22 degrees as shown in FIG. 6b. The interpolation function of the rotated curve in 0.01 cycle number increments is not shown.

DETAILED DESCRIPTION OF THE INVENTION

Figure 1:
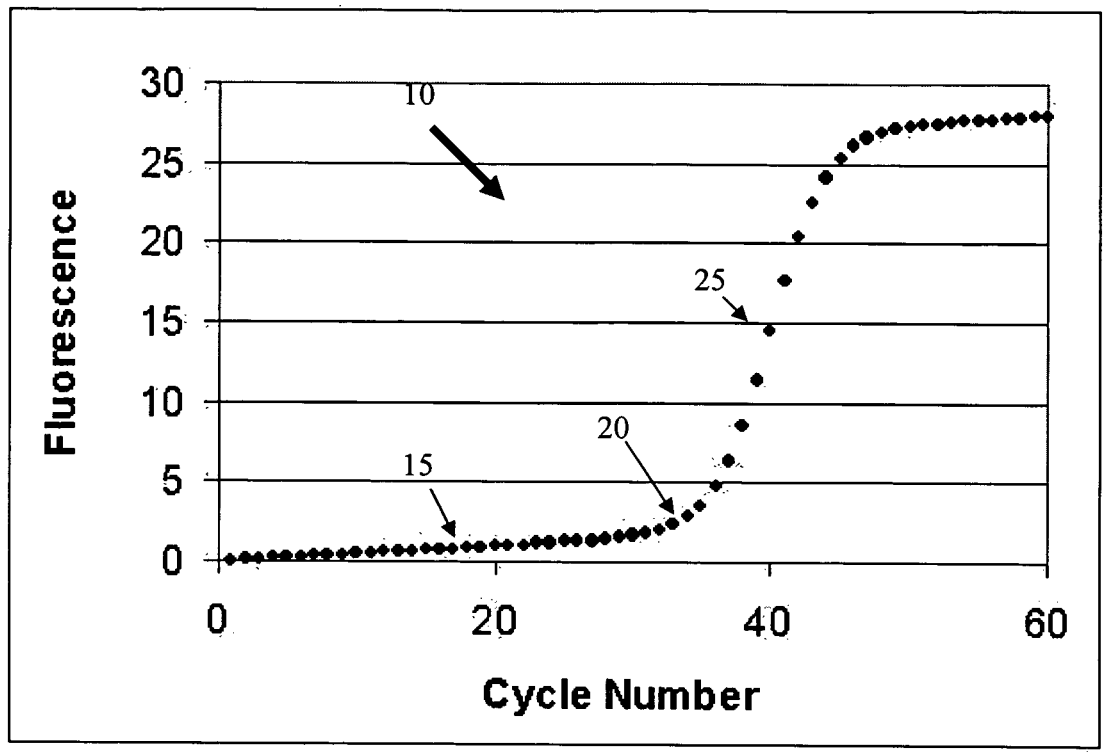
FIG. 1 illustrates an example of a typical PCR growth curve, plotted as fluorescence intensity vs. cycle number.

One example of an amplification curve 10 in the context of a kinetic PCR process is shown in FIG. 1. As shown, the curve 10 includes a lag phase region 15, and an exponential phase region 25. Such a curve includes a transitionary region of interest 20 linking the lag phase and the exponential phase. Region 20 is commonly referred to as the elbow or elbow region. The elbow region typically defines a transition in the growth or amplification rate of the underlying process, and identifying a specific transition point in region 20 can be useful for analyzing the behavior of the underlying process. In a typical PCR curve, identifying a transition point referred to as the elbow value or cycle threshold (Ct) value is extremely useful for understanding efficiency characteristics of the PCR process. Other processes that may provide similar sigmoid or growth curves include bacterial processes, enzymatic processes and binding processes. In bacterial growth curves, for example, the transition point of interest has been referred to as the time in lag phase, $\lambda$. Thus, although the remainder of this document will discuss the invention in terms of its applicability to PCR curves, it should be appreciated that the present invention may be applied to data curves related to these other processes.

As shown in FIG. 1, data for a typical PCR growth curve can be represented in a two-dimensional coordinate system, for example, with PCR cycle number defining the x-axis and an indicator of accumulated polynucleotide growth defining the y-axis. Typically, as shown in FIG. 1, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The definition of cycle can also include time, process cycles, unit operation cycles and reproductive cycles.

Figure 2:
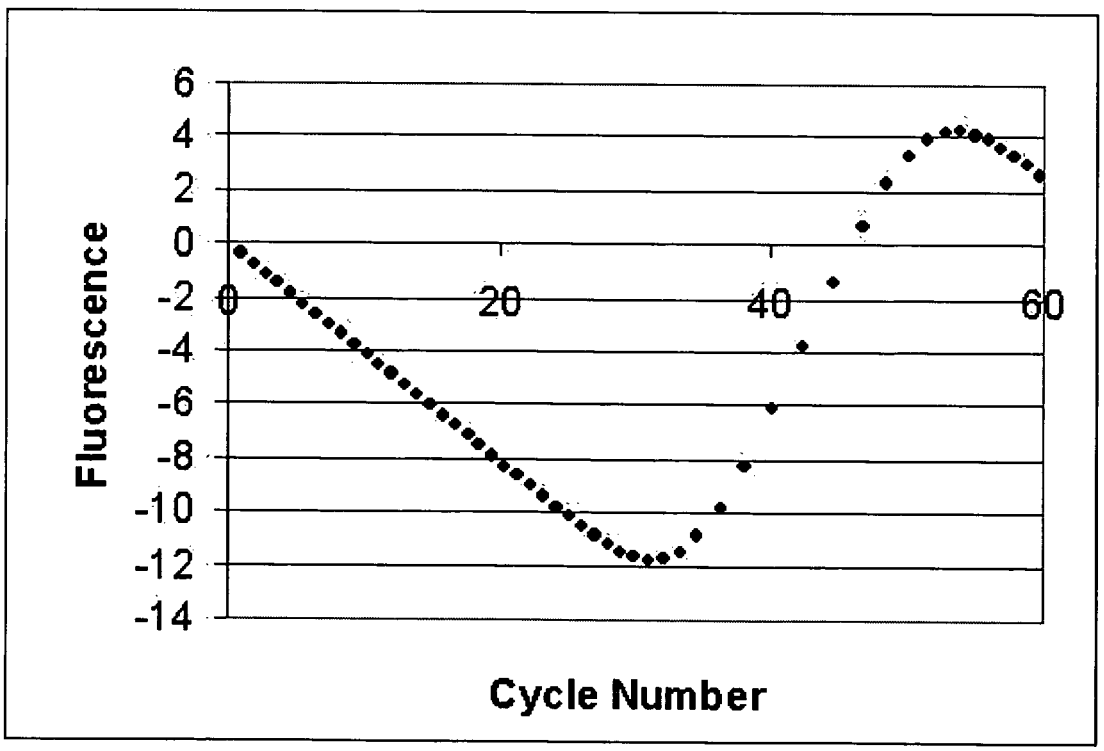
FIG. 2 shows the PCR growth curve data of FIG. 1 rotated by 25 degrees clockwise.
Figure 3:
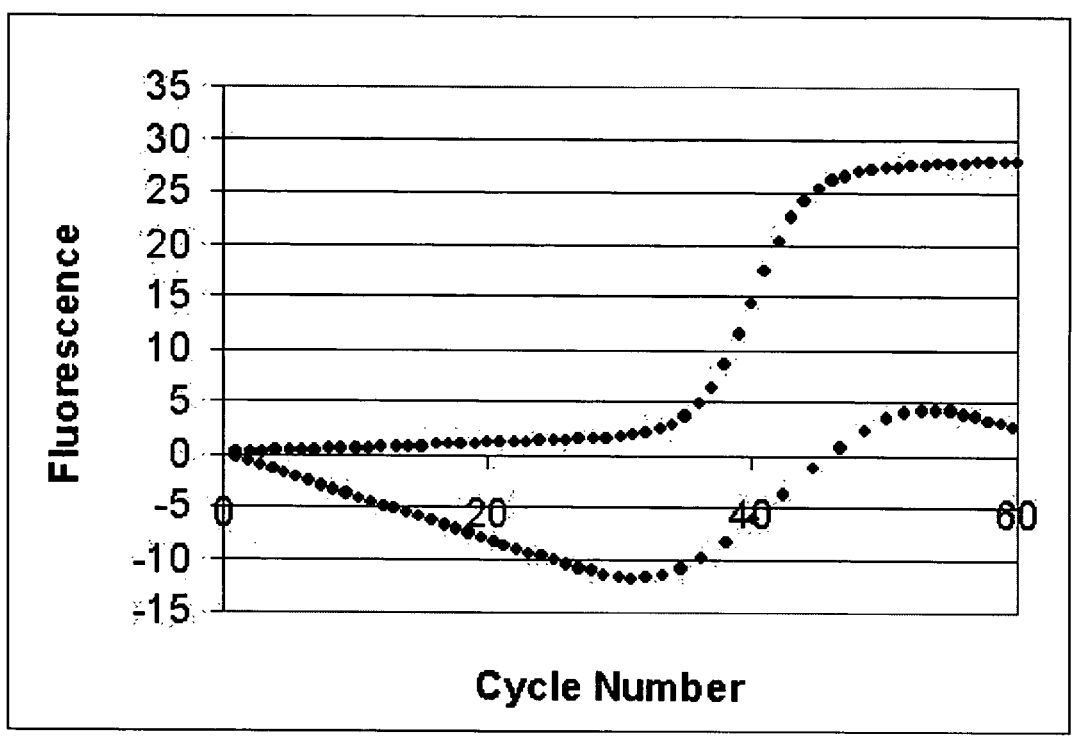
FIG. 3 shows a superposition of FIGS. 1 and 2.

According to the present invention, one embodiment of a process for determining a transitionary value in a sigmoid curve, such as the elbow value or Ct value of a kinetic PCR amplification curve, can be described briefly as follows. In a first operation, the experimental data set representing the amplification curve (e.g., fluorescence curve in FIG. 1) is rotated by an angle theta ($\theta$) so that the rotated data set forms a minimum in the region of the elbow. As an example, FIG. 2 shows the resulting data from FIG. 1 after rotation by 25 degrees clockwise relative to the origin coordinate. FIG. 3 shows a superposition of FIGS. 1 and 2. It is apparent from FIGS. 2 and 3 that by rotating the amplification curve in this manner, the search for the elbow becomes a much simpler task of identifying the location of the minimum in the rotated curve. Any data noise in the region prior to the elbow would have little influence, as the relevant parameter is the minimum in the curve. In subsequent operations, at least the data point in the transformed data set representing the minimum is rotated back by an angle –theta ($-\theta$), and one or both of the resulting coordinate values (fluorescence and cycle number) representing the elbow or Ct value are output or displayed. In other aspects, additional data points can be interpolated between the experimental data points to provide fractional elbow values as will be described in more detail below. Such interpolation may be performed before or after the first rotational transformation operation. It should be appreciated that the data set may initially be rotated clockwise or counter-clockwise so that the rotated data set forms a minimum or a maximum in the region of the elbow. The subsequent (inverse) rotation transform may then rotate one or more data points in the rotated data set back to the original data set orientation, e.g., counterclockwise or clockwise by the reverse angle. In general, the inverse transform may be performed in any manner that returns the orientation of the data point(s) back to the original visual orientation. Further, the rotation transforms may rotate the data set about any arbitrary line or data point, however rotation about the origin coordinate is preferred.

Figure 4:
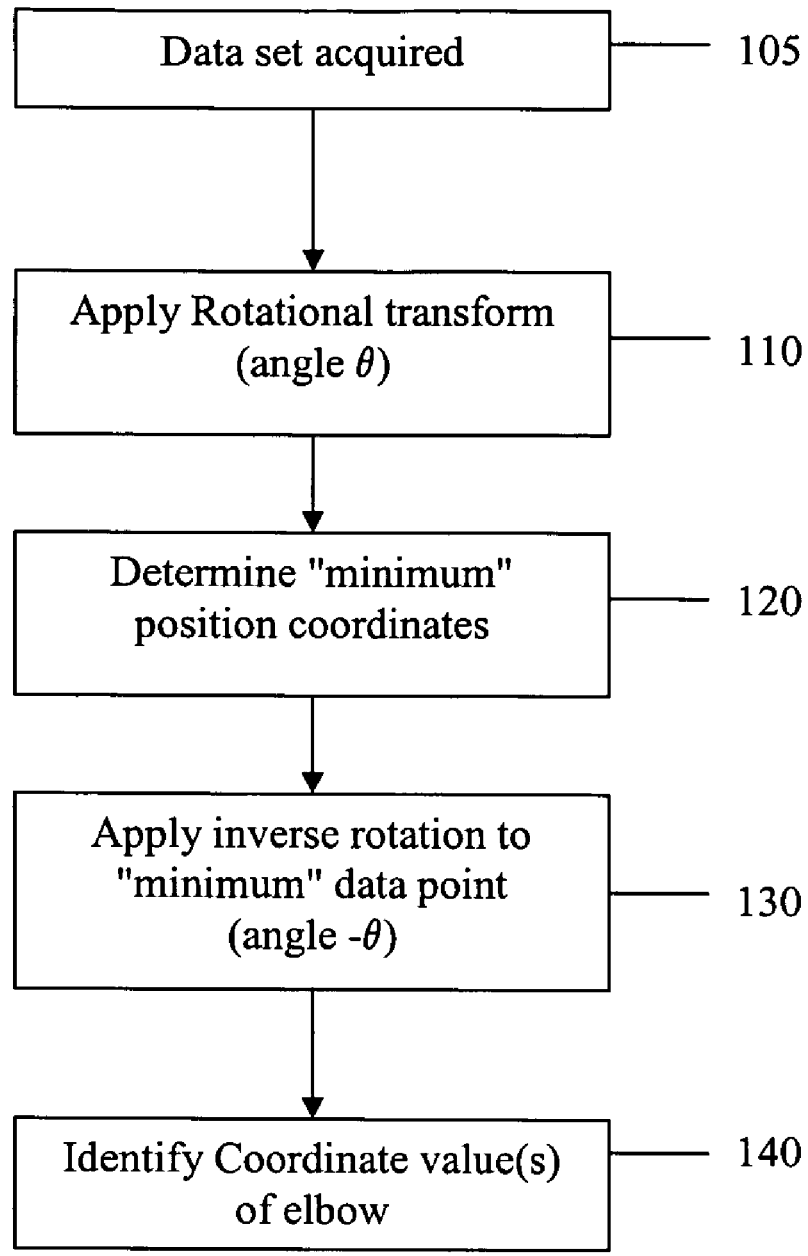
FIG. 4 illustrates a process for determining the elbow value for a PCR process according to one embodiment.

A process for determining the elbow value in a kinetic PCR curve according to one embodiment is shown in FIG. 4. In step 105, the data set is acquired. In the case where the determination process is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the module after the experiment has been completed. Similarly, the data set may be provided to a separate system such as a desktop computer system via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. After the data set has been received or acquired, in step 110 a rotational transformation is applied to at least a portion of the data set containing the elbow, so as to rotate the data set by an angle theta ($\theta$). In step 120, the minimum position coordinate in the rotated data set is determined. In step 130, an inverse rotation transformation of this point is performed by rotating in the opposite direction by the angle $-\theta$ to give the final coordinates of the elbow. It should be appreciated that other data points, in addition to the "minimum" data point determined in step 120, may be rotated in step 130. In step 140, one or both of the re-determined coordinate values of the identified elbow point are returned, e.g., output or displayed. The following example illustrates the process: In FIG. 2 (rotated data set), the minimum point is at coordinates (30.92,−11.79). This point is then rotated by −25 degrees (counter-clockwise) to give the final coordinates of (33.0, 2.38). Thus, the elbow is determined to be 33.0 (cycle number).

It should be appreciated that the Ct determination process may be implemented in computer code running on a processor of a computer system. The code includes instructions for controlling a processor to implement various aspects and steps of the determination process. The code is typically stored on a hard disk, RAM or portable medium such as a CD, DVD, etc. Similarly, the process may be implemented in a PCR device such as a thermocycler including a processor executing instructions stored in a memory unit coupled to the processor. Code including such instructions may be downloaded to the PCR device memory unit over a network connection or direct connection to a code source or using a portable medium as is well known.

In one preferred aspect, each rotation transformation rotates the data points about the origin (0,0), however, the data may be rotated about any coordinate as desired. Additionally, the data set may initially be rotated in a different manner, for example counterclockwise by an angle −(180°−0) or clockwise by an angle (180°+0) in step 110. In this case, the relevant determination in step 120 is to determine the "maximum" value. Thus, it should be appreciated by one skilled in the art that other rotational transform parameters will allow for identification of the elbow value.

Figure 5:
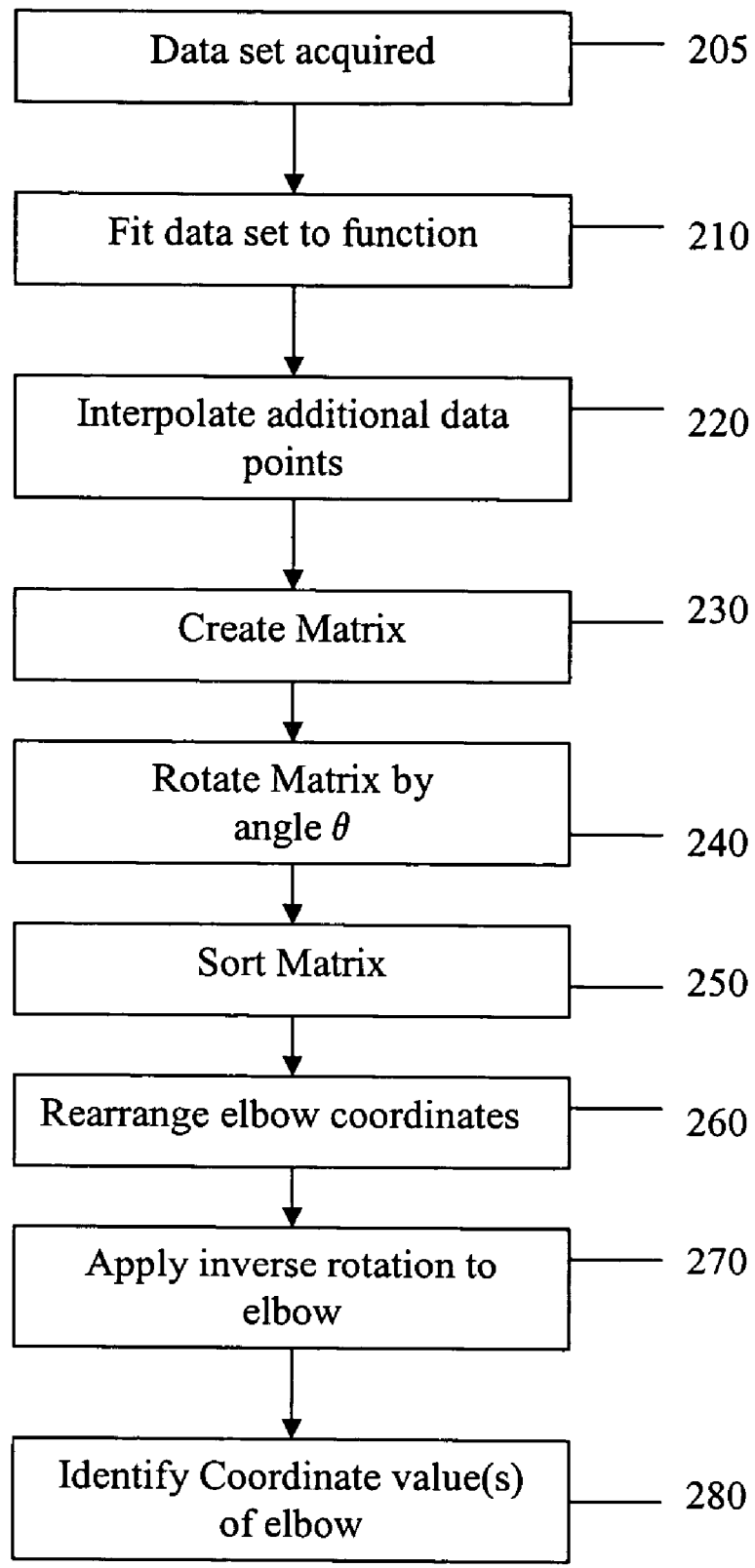
FIG. 5 illustrates a process for determining the elbow value for a PCR process according to another embodiment.

A process for determining the elbow value in a kinetic PCR process according to another embodiment is shown in FIG. 5. After the data set has been received or acquired in step 205, in step 210, a function such as a cubic spline function is fit to the data points. This may be done using the software application Mathematica® or other application. In optional step 220, data points are interpolated between existing data points at cycle intervals of 1.0 or less, e.g., 0.05 or 0.01. In step 230, a matrix of data points (x,y) is created of the (interpolated fluorescence, cycle numbers). This large matrix of numbers, or a portion thereof, is then rotated by an angle theta ($\theta$) in step 240 and coordinates are exchanged to give coordinates (y',x'). In step 250, this (rotated) matrix is sorted in ascending order of fluorescence values. In this manner, the data point having the minimum fluorescence value is determined by identifying the data point in the first position. The (y',x') coordinates of the first position in the sorted matrix corresponds to the rotated elbow. In step 260, this minimum (y',x') is then rearranged as (x',y') and in step 270, the inverse rotation of this single point by angle −theta ($-\theta$) is performed to give the elbow value. It should be appreciated that the inverse rotation may be applied to additional points near this single point. Also, as above, it should be understood that interpolation of additional data points (optional step 220) may be performed before or after application of the rotational transformation in step 240. Further, as above, different rotational angles and directions may be used, and sorting may be used to identify a "maximum" where appropriate. In step 280, one or both of the coordinate values of the elbow point are returned, e.g., output or displayed.

An example of Mathematica code configured to perform the operations on a vector yd of fluorescence values is shown below:

```
Needs ["Geometry 'Rotations'"]
CtRot[yd_,theta_]:=Module[{data,vec,ni,rotp,x,y,rt},
    data=Table[{i,yd[[i]]},{i,1,Length[yd]}];
    vec=Table[{i,1},{i,1,Length[data]}];
    For[i=1,i<=Length[data],i++,
        vec[[i]]=Rotate2D[{data[[i,1]],data[[i,2]]},theta Degree,{0,0}]
    ];
    IntF=Interpolation[vec];
    mind=Ceiling[vec[[1]][[1]]];
    maxd=Floor[vec[[Length[vec]]][[1]]];
    rotp2=Sort[Table[{IntF[x],x},{x,mind,maxd,0.01}]][[1]];
    rotp={rotp2[[2]],rotp2[[1]]};
    rt=Rotate2D[rotp,-theta Degree,{0,0}];
    rt[[1]]]
```

One skilled in the art should appreciate that the elbow determination processes of the present invention can be coded using a variety of programming languages such as C, C+, Fortran, VisualBasic, etc., as well as applications similar to Mathematica which provide pre-packaged routines, functions and procedures useful for data visualization and analysis. Another example of the latter is MATLAB®.

FIG. 6 shows an example of a data set for an amplification curve processed according to the present invention. FIG. 6c is a table including 1) the data set values (cycle number and fluorescence intensity) of the amplification curve shown visually in FIG. 6a, and 2) the values of the transformed cycle number and fluorescence intensity when a 22 degree rotation transform has been applied as shown visually in FIG. 6b. As shown, when rotated by 22 degrees, the coordinates of the minimum in the rotated curve (FIG. 6b) is (20.18, −5.852). When these coordinates are rotated back by 22 degrees, the coordinates of the elbow or Ct value are determined to be (20.90, 2.13). The determined Ct value is 20.90 cycles.

The fact that the minimum in the rotated data set can be determined in one aspect using a sorting method advantageously eliminates the need to take derivatives. This is an advantage as the first and especially the second derivatives that are often used in determining the elbow are extremely sensitive to noisy data. It will be appreciated, however, that other methods may be used to identify the point having the minimum fluorescence intensity value in the rotated data set. For example, an algorithm that searches for and locates the minimum value may be used. Useful algorithms include a method of sharpest descent algorithm, a conjugate gradient method, a Levenberg-Marquardt method and an order statistic method. These and other useful algorithms can be found in software applications such as Mathematica, or could be readily coded by one skilled in the art.

Thus, the present invention advantageously eliminates problems found in previous algorithms, for example: (1) noisy, spike data, (2) variable baselines, (3) high baselines, (4) sensitivity of derivative methods, and (5) need for a large number of parameters. The processes of the present invention are particularly useful in PCR systems, such as thermocyclers, to significantly improve the quality of the PCR results data.

According to one embodiment, a methodology to optimize the rotation transforms applied, for example, in steps 110 (FIG. 4) and 240 (FIG. 5), is provided. According to one aspect, optimization of the rotation angle $\theta$ is performed by minimization of the Coefficient of Variation (Cv) of Ct values predicted at target titer values.

The rotation transform algorithm described above uses a single parameter of rotation angle ($\theta$) to determine the Ct (elbow) in kinetic PCR. This algorithm thus provides a framework where the quality of the parameter fit can be optimized. According to the present invention, the problems associated with optimizing parameters associated with other methodologies are advantageously eliminated by optimizing the single parameter that this algorithm uses: rotation angle. In one aspect, this is done by providing a rigorous mathematical method to optimize the rotation angle. In particular, according to one aspect of the present invention the coefficient of variation (Cv) of Ct values at target titer values is minimized to provide an optimal rotation angle. An example follows.

Figure 7:
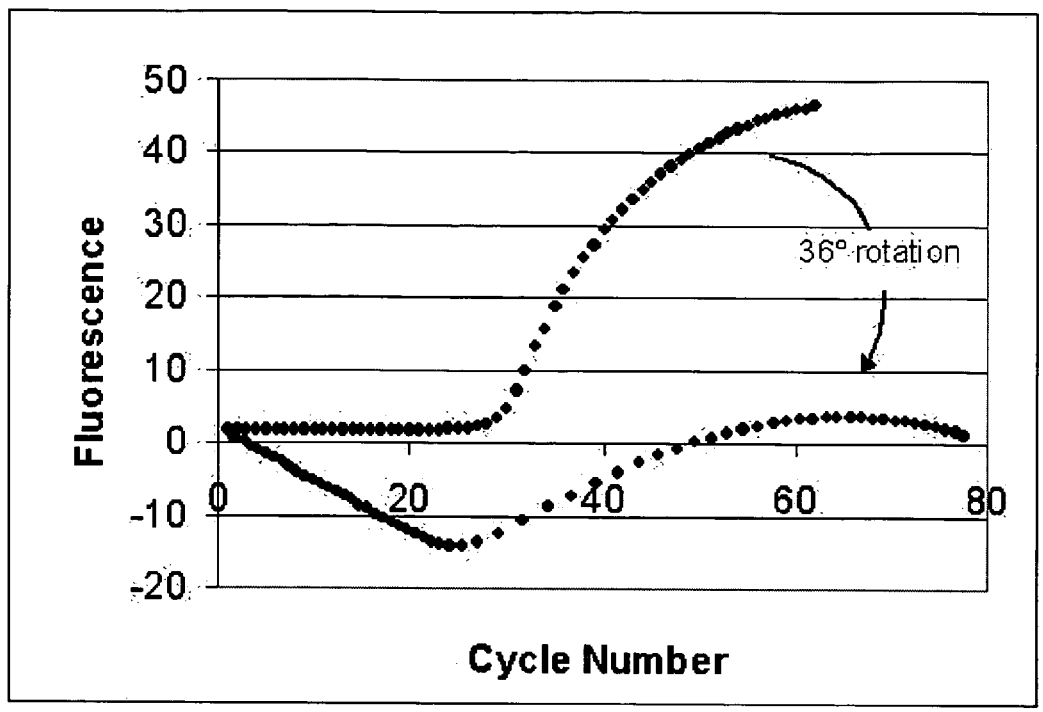
FIG. 7 shows an example of a single data set of an HCV assay plotted in a two-dimensional graph.

Kinetic PCR was performed on Hepatitis C Virus (HCV) RNA at different titer input values to produce a plurality of kinetic PCR amplification curves. Study was set up with 22 replicates each having HCV RNA titers at $10^3$, $10^4$, $10^5$, and $10^7$ c/mL and 8 replicates of negative control at 0 c/mL HCV RNA. The series of HCV amplification curves were analyzed by determining the Ct values at a rotation of 36 degrees. This angle was subjectively selected based on prior experiments. FIG. 7 shows an example of a data set of one of these assays plotted in a two-dimensional graph. At each titer value, the standard deviation of the Ct values divided by the average of the Ct values is taken. This gives the % Coefficient of Variation (% CV) value for each titer, resulting in 4% CV values (one at each titer, the 0 titer being ignored). The average of these 4% CV values is then determined. The average % CV serves as a single variable to optimize. The % CV at low titer may be more important. For example, when someone has a high amount of virus in their systems the drug dosages may be maximized. The low titer is where precision is really needed to help balance the toxicity/efficacy effect. Thus, another option is to optimize the rotation angle at the minimum titer value.

Figure 8:
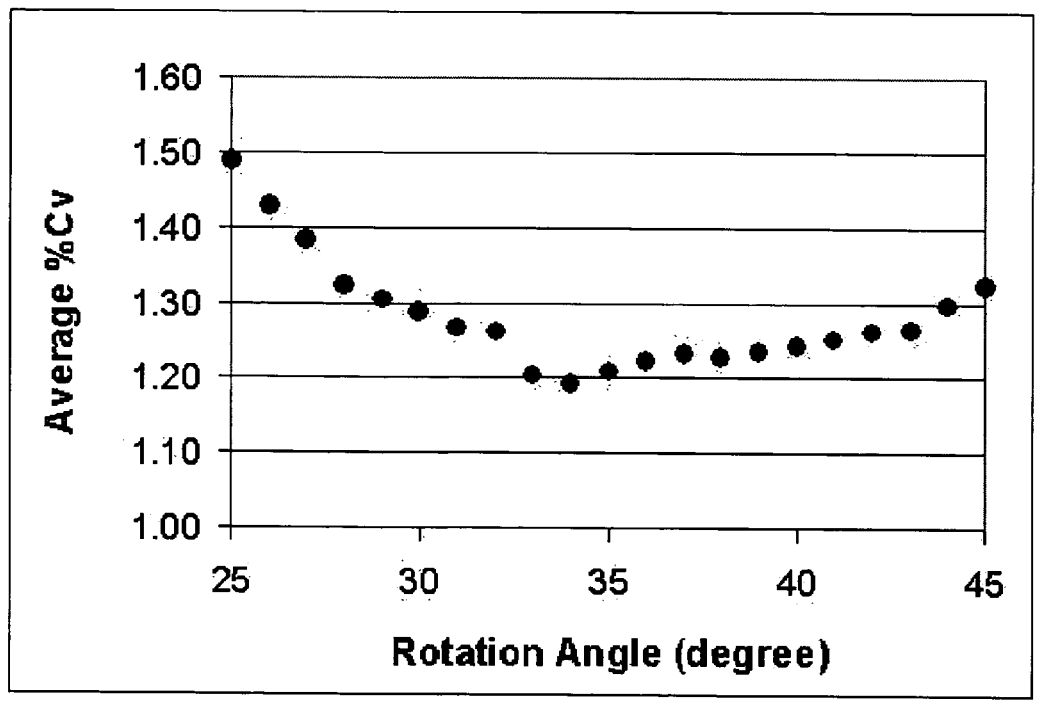
FIG. 8 shows the average Cv plotted vs. rotation angle in single increments of 1 degree for the HCV assay of FIG. 7.
Figure 9:
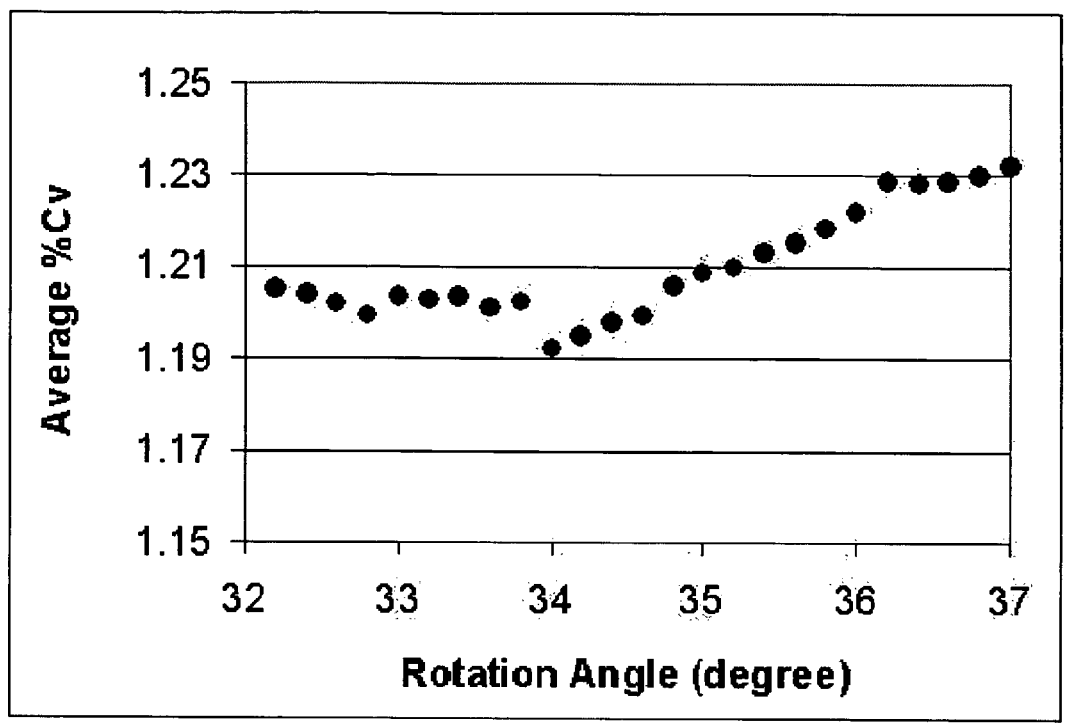
FIG. 9 shows a region from FIG. 8 expanded in increments of 0.2 degrees.

Accordingly, the analysis process is repeated at different rotation angles, for example at 1 degree increments. FIG. 8 shows the average % CV plotted vs. rotation angle in single increments of 1 degree for this HCV study. From FIG. 8, it is apparent that the minimum occurs in the region near 32-37 degrees. This region is then expanded in increments of 0.2 degrees and is plotted in FIG. 9. FIG. 9 indicates that the minimum average % CV is at 34 degrees, with a value of 1.19%, with individual values of the 4 CV of 0.97%, 0.86%, 1.4%, and 1.5%, corresponding to titers of at $10^3$, $10^4$, $10^5$, and $10^7$ c/mL, respectively.

Figure 10:
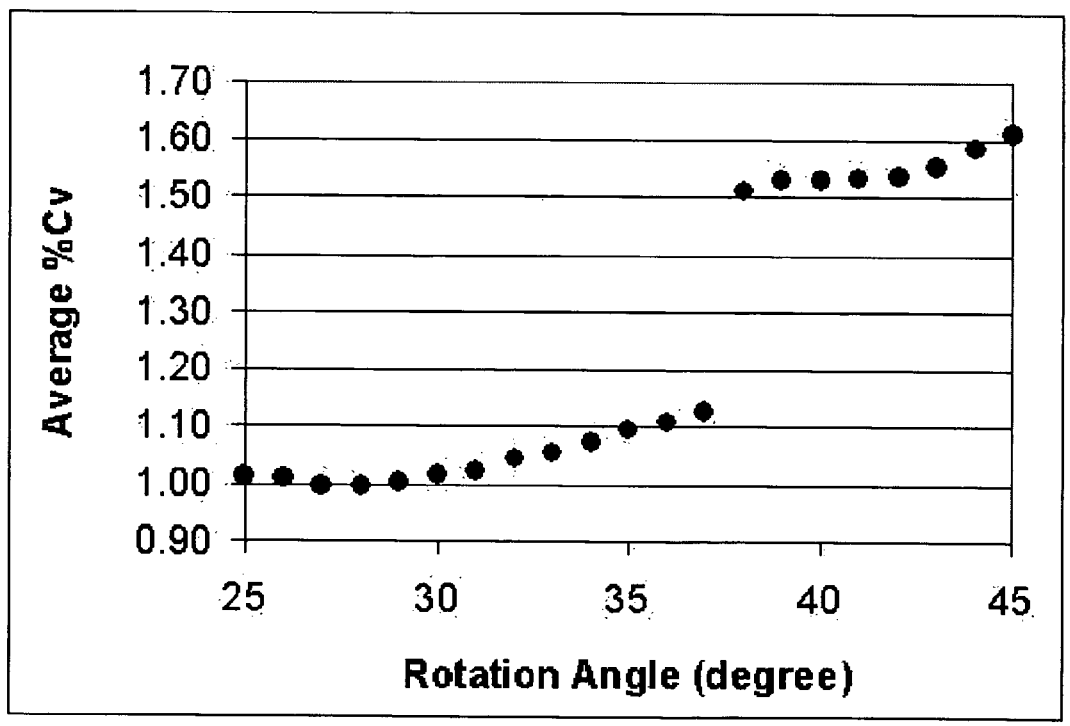
FIG. 10 shows a plot of the average Cv vs. rotation angle between 25 and 45 degrees in 1 degree increments when using normalized data for the HCV assay of FIGS. 7 and 8.
Figure 11:
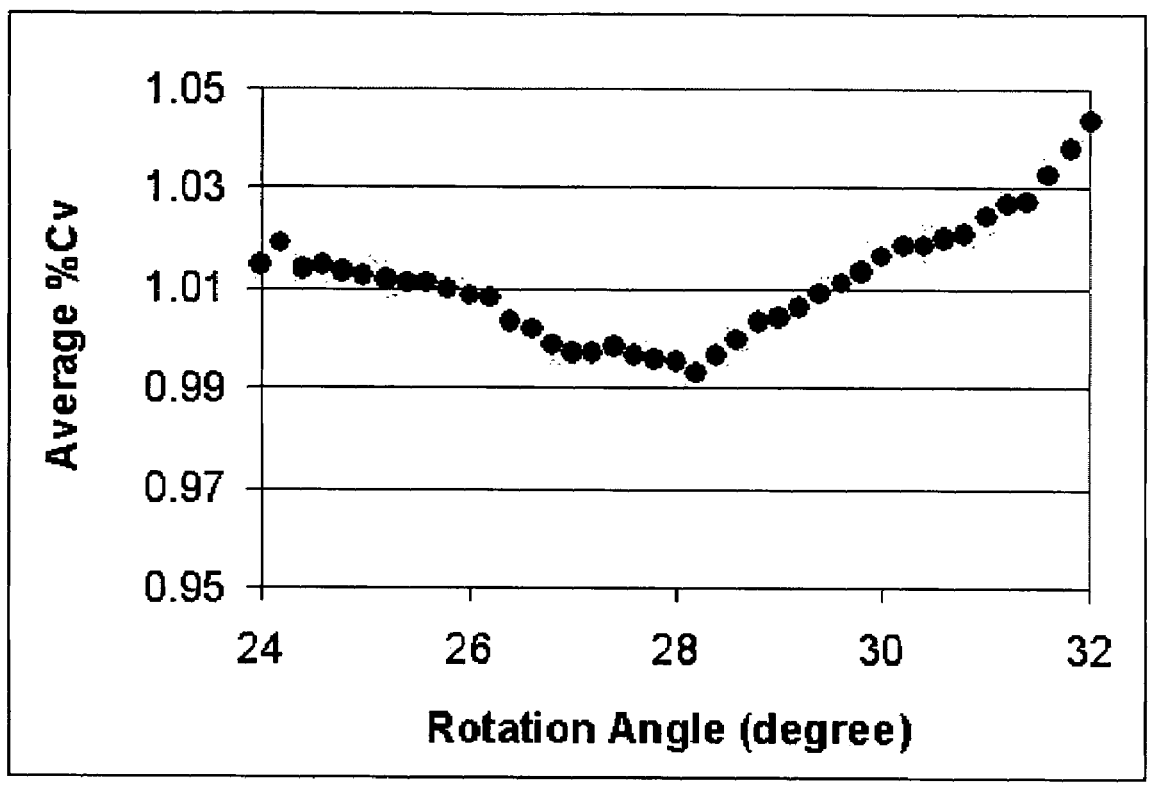
FIG. 11 shows an expansion of the data of FIG. 10 between 24-32 degrees in 0.2 degree increments.

In one aspect, the data is normalized prior to being processed through the rotational algorithm. Applying pre-rotation normalization to the HCV analysis example results in an average % CV of 0.99% and % CV values at the respective titers of 0.67%, 0.79%, 1.28%, and 1.22%. A plot of the average % CV vs. rotation angles between 25 and 45 degrees in 1 degree increments when using the normalized data is shown in FIG. 10. In this case, the minimum in the curve occurs in the range 25-35 degrees. Accordingly, FIG. 11 shows an expansion of the data between 24-32 degrees in 0.2 degree increments. As can be seen, the minimum occurs at an angle of 28.2 degrees.

It should be appreciated that other assay parameters can be utilized to optimize the rotation angle. Examples include titer precision, accuracy, and hit rate with, for example, a 95% confidence interval, minimizing the number of false positives, or minimizing the number of false negatives. It should also be appreciated that the processes described above may be implemented in a variety of analytical instruments and systems where the underlying data acquisition process may produce sigmoid curves similar to PCR amplification curves.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, throughout the document, the rotation is described in a 2D visual graph system. However, it should be appreciated that a data set may be processed and visualized in any n-dimensional space. For example, the data may be visualized or plotted in a 3D system (e.g., with some arbitrary third dimensional coordinate), and then the rotation transforms performed with rotation around any axis or coordinate point as desired. Therefore, the scope of the appended claims should be accorded the broadest interpretation so as to encompass all such modifications and similar arrangements.

What is claimed is:

1. A computer-implemented method of determining the elbow or cycle threshold (Ct) value in a region of a Polymerase Chain Reaction (PCR) data curve, the method comprising the steps all of which are, implemented in a computer system having a processor, of:

receiving a PCR data set representing a PCR data curve, said data set including a plurality of data points each having a pair of coordinate values, wherein if viewed in a two-dimensional coordinate system the data set has a region of interest;

applying a first rotational transformation to at least a portion of the data set including the region of interest comprising an elbow or cycle threshold (Ct) value to produce a transformed data set;

identifying a data point in the transformed data set having at least one of a minimum coordinate value or a maximum coordinate value;

applying a second rotational transformation, inverse to the first transformation, to the identified data point; and thereafter re-determining at least one coordinate value of the identified data point, wherein the re-determined coordinate value of the identified data point represents the Ct value in the PCR data curve.

2. The method of claim 1, wherein the pair of coordinate values represent an accumulation of amplified polynucleotide and a cycle number.

3. The method of claim 2, wherein the accumulation of amplified polynucleotide is represented by one of a fluorescence intensity value, a luminescence intensity value, a chemiluminescence intensity value, a phosphorescence intensity value, a charge transfer value, a bioluminescence intensity value, or an absorbance value.

4. The method of claim 1, further including interpolating additional data points using at least the data points in the region of interest.

5. The method of claim 4, wherein interpolating is performed before applying the first rotational transformation.

6. The method of claim 4, wherein interpolating is performed after applying the first rotational transformation.

7. The method of claim 4, wherein interpolation is performed to produce data points at an incremental scale of about 1.0 or less per coordinate interval along one of said coordinates.

8. The method of claim 1, wherein the first rotational transformation rotates the coordinate values of said portion of the data set clockwise or counterclockwise by an angle $\theta$ relative to a selected coordinate value.

9. The method of claim 8, wherein the second rotational transformation rotates the coordinate values of the first data point by an angle $-\theta$ relative to the selected coordinate value.

10. The method of claim 8, further comprising determining an optimum angle $\theta$ based on values of an assay parameter for a plurality of assays.

11. The method of claim 10, wherein determining said angle $\theta$ includes determining the angle at which a coefficient of variation of cycle threshold (Ct) values for a plurality of angles at one or more titer values is minimized.

12. The method of claim 1, further comprising providing the Ct value as an output.

13. The method of claim 1, further comprising displaying the Ct value in a two dimensional coordinate system on a display device.

14. The method of claim 1, further comprising displaying said first data set in a two dimensional coordinate system on a display device.

15. The method of claim 1, wherein identifying includes sorting the coordinate values of the data points in the transformed data set to determine a data point having at least one minimum coordinate value.

16. The method of claim 1, wherein identifying includes taking a derivative of the transformed data set.

17. A tangible computer readable medium that stores code for controlling a processor to determine a cycle threshold (Ct) value in a kinetic Polymerase Chain Reaction (PCR) amplification curve, the code including instructions to:
receive a data set representing a kinetic PCR amplification curve, said data set including a plurality of data points each having a pair of coordinate values, wherein said data set includes data points in a region of interest which includes the Ct value;
apply a first rotational transformation to at least the portion of the data set including the region of interest to produce a transformed data set;
identify a data point in the transformed data set having at least one of a minimum coordinate value or a maximum coordinate value;
apply a second rotational transformation, inverse to the first transformation, to the identified data point; and thereafter
re-determine at least one coordinate value of the identified data point, wherein the re-determined coordinate value of the identified data point represents the Ct value for the PCR curve.

18. A real-time Polymerase Chain Reaction (PCR) system, comprising:
a PCR analysis module that generates a PCR data set representing a PCR amplification curve, said data set including a plurality of data points each having a pair of coordinate values, wherein said data set includes data points in a region of interest which includes a cycle threshold (Ct) value; and
an intelligence module adapted to process the PCR data set to determine the Ct value by:
applying a first rotational transformation to at least the portion of the data set including the region of interest to produce a transformed data set;
identifying a data point in the transformed data set having at least one minimum coordinate value;
applying a second rotational transformation, inverse to the first transformation, to the identified data point; and thereafter
re-determining at least one coordinate value of the identified data point, wherein the re-determined coordinate value of the identified data point represents the Ct value for the PCR curve.

19. The method of claim 10, wherein determining said angle $\theta$ includes determining the angle at which a coefficient of variation of cycle threshold (Ct) values for a plurality of angles at a minimum titer value is minimized.

20. The method of claim 10, wherein determining said angle $\theta$ includes using one or more parameters selected from the group consisting of titer precision, accuracy, hit rate, minimization of a number of false positives, and minimization of a number of false negatives to optimize said angle $\theta$.

21. A real-time Polymerase Chain Reaction (PCR) system, comprising:
a PCR data acquisition device that generates a PCR data set representing a PCR amplification curve, said data set including a plurality of data points each having a pair of coordinate values, wherein said data set includes data points in a region of interest which includes a cycle threshold (Ct) value; and
a processor adapted to receive and to process the PCR data set to determine the Ct value by:
applying a first rotational transformation to at least the portion of the data set including the region of interest to produce a transformed data set;
identifying a data point in the transformed data set having at least one minimum coordinate value;
applying a second rotational transformation, inverse to the first transformation, to the identified data point; and thereafter
re-determining at least one coordinate value of the identified data point, wherein the re-determined coordinate value of the identified data point represents the Ct value for the PCR curve.

* * * * *